United States Patent [19]

Katsuhara et al.

[11] Patent Number: 4,564,716

[45] Date of Patent: Jan. 14, 1986

[54] PREPARATION OF 1,1,1,3,3,3-HEXAFLUOROPROPANE-2-OL BY HYDROGENOLYSIS OF HEXAFLUOROACETONE HYDRATE

[75] Inventors: Yutaka Katsuhara, Kawagoe; Toshihiro Nakamichi, Kamifukuoka; Toshikazu Kawai, Kawagoe; Toru Nakazora, Saitama, all of Japan

[73] Assignee: Central Glass Company, Limited, Ube, Japan

[21] Appl. No.: 654,876

[22] Filed: Sep. 27, 1984

[30] Foreign Application Priority Data

Sep. 27, 1983 [JP] Japan .................... 58-177017

[51] Int. Cl.$^4$ ............................ C07C 31/38
[52] U.S. Cl. .................................. 568/842
[58] Field of Search ........................ 568/842

[56] References Cited

U.S. PATENT DOCUMENTS 2,824,897  2/1958  Wujciak .................. 568/842
3,418,337  12/1968  Middleton ............... 568/842
3,607,952  9/1971  Lee ........................ 568/842
4,467,124  8/1984  Kawai et al. .

FOREIGN PATENT DOCUMENTS 2113551  10/1972  Fed. Rep. of Germany .
965048  7/1964  United Kingdom .
2087383  5/1982  United Kingdom .

*Primary Examiner*—Howard T. Mars
*Attorney, Agent, or Firm*—Fleit, Jacobson, Cohn & Price

[57] ABSTRACT

1,1,1,3,3,3-hexafluoropropane-2-ol is prepared easily and efficiently by gas-liquid reaction between hydrogen gas and a hexafluoroacetone hydrate such as trihydrate, which is liquid at room temperature, using a suitable catalyst such as active carbon-palladium catalyst. Preferably the gauge pressure of hydrogen gas is 2–10 kg/cm$^2$, and the hydrogenolysis reaction temperature is 70°–100° C. The life of the catalyst can be prolonged by the addition of a small quantity of sodium hydroxide. The addition of a small quantity of aluminum hydroxide is effective in suppressing the formation of fluorine ions in the reaction liquid.

12 Claims, No Drawings

PREPARATION OF 1,1,1,3,3,3-HEXAFLUOROPROPANE-2-OL BY HYDROGENOLYSIS OF HEXAFLUOROACETONE HYDRATE

BACKGROUND OF THE INVENTION

This invention relates to a process of preparing 1,1,1,3,3,3-hexafluoropropane-2-ol by catalytic hydrogenolysis of hexafluoroacetone hydrate in liquid phase.

As is known, 1,1,1,3,3,3-hexafluoropropane-2-ol $(CH_3)_2CHOH$ (also called hexafluoroisopropanol: so, herein abbreviated to HFIP) is useful as a solvent having peculiar dissolving capabilities and also serves as an intermediate material for various compounds including medicines, anesthetics and agricultural chemicals.

HFIP can be prepared from hexafluoroacetone (abbreviated to HFA) by a reduction or hydrogenation reaction. For example, liquid phase reduction of HFA using sodium boron hydride or lithium aluminum hydride as catalyst gives HFIP. However, this method is not suited to industrial applications. Another method is liquid phase hydrogenation of HFA in the presence of a noble metal catalyst. However, the reactor for use in this method is required to withstand very high pressures (e.g. of the order of 50 kg/cm$^2$) since the reaction must be carried out under high pressures sufficient to keep HFA (b.p. $-28°$ C.) in liquid phase at the reaction temperature.

Still another method is vapor phase catalytic hydrogenation of HFA. In this case the hydrogenation reaction can continuously be carried out at substantially the atmospheric pressure by passing HFA vapor and hydrogen gas through a catalyst column. However, it is difficult to control the reaction temperature, and undesirable hot spots are often produced in the catalyst column because of generation of heat in the hydrogenation reaction. Furthermore, it is inevitable that the activity of the packed catalyst lowers with the lapse of time, and therefore it is necessary to carry out troublesome procedures for examining possible changes in the quality of the product with the lapse of time and for adjustment of the reaction conditions. Besides, usually it is necessary to use hydrogen gas in considerable excess of the theoretical quantity with a view to accomplishing sufficient conversion of HFA into HFIP. Loss of the excess portion of hydrogen gas leads to a rise in the production cost, but recovery of excess hydrogen gas requires the provision of extra apparatus.

HFA used as the starting material in the above described known processes is a noxious compound which exists as a gas at room temperature. Accordingly, in industrial preparation of HFIP by a conventional method extreme care must be taken in storing, handling and transporting HFA.

As a solution for inconveniences of using gaseous HFA, Japanese patent application primary publication No. 57-81424 and corresponding British patent application publication No. 2,087,383A have proposed to prepare HFIP by vapor phase hydrogenolysis of a hydrate of HFA such as HFA trihydrate, which is liquid at room temperature, using a nickel or palladium catalyst. However, this method too has the disadvantages described above with respect to the vapor phase hydrogenation of HFA (anhydrous).

SUMMARY OF THE INVENTION

It is an object of the present invention to provide a novel process of preparing HFIP, which is more convenient for industrial practice than the known processes and is very high in the efficiency of conversion of the starting materials into HFIP.

A process according to the invention is for the preparation of HFIP and comprises the step of making hydrogen gas contact with a HFA hydrate in liquid phase in the presence of a catalyst which is active for hydrogenolysis of HFA hydrates into HFIP.

A preferred example of the catalyst is an active carbon-palladium catalyst. The catalyst is put into the HFA hydrate liquid, and hydrogen gas is brought into contact with the HFA hydrate at a relatively low pressure such as a gauge pressure of 2-10 kg/cm$^2$. The reaction proceeds smoothly at moderately elevated temperatures such as about 70°–100° C.

A hydrate of HFA is readily obtained by absorption of HFA in water, and the degree of hydration can be controlled over a relatively wide range. It is also possible to direclty prepare a hydrate of HFA without handling anhydrous HFA as intermediate. HFA rapidly undergoes equimolar reaction with water to form HFA monohydrate, which is a gem-diol compound of the structural formula $(CF_3)_2C(OH)_2$ and is solid at room temperature (m.p. 46° C.). This monohydrate readily dissolves in excess water and turns into higher hydrates. Where the mole ratio of water to HFA is approximately 3:1, the resultant liquid is an azeotropic composition having a boiling point of 106° C. Hydrates of HFA are expressed by the general formula $(CF_3)_2C(OH)_2 \cdot xH_2O$, where x is zero or a positive number which need not be an integer. For example, the formula represents HFA monohydrate when x=0 and HFA trihydrate when x=2.

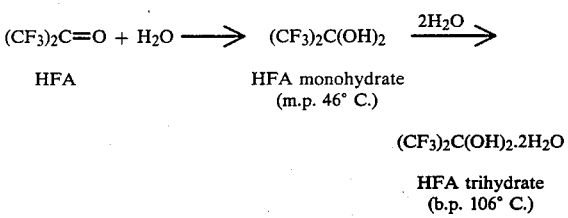

When x in the above general formula is larger than 0.5 the hydrate of HFA are all stable liquid at room temperature. Such hydrates of HFA are very convenient for storage and transportation and suitable for use in the present invention. The above formulas show that hydrates of HFA are clearly different from anhydrous HFA in chemical structure and, hence, in chemical and physical properties.

A catalytic hydrogenolysis reaction in a process according to the invention is represented by the following equation.

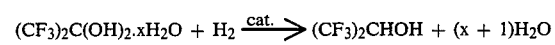

Where x is larger than 0.5, this reaction is carried out by forcing hydrogen gas to be absorbed in the liquid phase hydrate of HFA with the catalyst dispersed in the liquid phase, and the product of the reaction is an aqueous solution of HFIP. This process is very favorable for industrial practice because the liquid starting material is convenient for handling and also because the gas-liquid reaction rapidly proceeds at relatively low pressures of hydrogen gas and at moderately elevated temperatures. Furthermore, HFIP is obtained with good yields.

The life of the catalyst used in this process can be prolonged by the addition of a very small quantity of sodium hydroxide to the HFA hydrate.

In this reaction a very small portion of the HFA hydrate will undergo excessive hydrogenolytic decomposition to result in the presence of fluorine ions, though in very low concentrations, in the reaction liquid. We have found that the formation of fluorine ions can efficiently be suppressed by adding a very small amount of aluminum hydroxide to the HFA hydrate in advance.

The product of the process according to the invention is essentially a mixture of HFIP and water, which will possibly contain unreacted HFA hydrate and/or small amounts of some by-products. Fractional refinement of this crude HFIP can easily and efficiently be accomplished by a usual atmospheric distillation method, and it is easy to obtain HFIP of 99.99% or higher purity.

DESCRIPTION OF THE PREFERRED EMBODIMENTS

As the hydrogenolysis catalyst for use in the present invention, a catalyst comprising metallic palladium as the principal catalytic component is particularly effective. It is preferred to use a catalyst comprising metallic palladium carried on active carbon. It is suitable that the content of Pd in such a catalyst is about 2-5% by weight as is usual in conventional active carbon-palladium catalysts. Second to a palladium catalyst, a catalyst comprising metallic nickel as the principal catalytic component is effective and fully practicable. Also it is possible to use a platinum catalyst, rhodium catalyst or ruthenium catalyst.

In our process a preferred range of the hydrogen gas pressure is from 2 to 10 $kg/cm^2$ by gauge pressure. When the hydrogen gas pressure is below 2 $kg/cm^2$ the rate of the reaction is not so high, and the actual pressure of hydrogen gas further lowers as the reaction proceeds because HFIP (b.p. 58° C.) formed by the reaction has a considerable vapor pressure at the reaction temperature (usually 70°-100° C.). Therefore, when the hydrogen gas pressure is below 2 $kg/cm^2$ it takes a very long time to complete the hydrogenolysis of a batch of a HFA hydrate. The rate of the reaction becomes higher as the hydrogen gas pressure is made higher and usually reaches a practically sufficient level at a hydrogen gas pressure of 5-6 $kg/cm^2$ (gauge pressure). It is possible to make the hydrogen gas pressure higher than 10 $kg/cm^2$ to thereby complete the reaction in a very short time, but in that case there arises the need of using a special pressure vessel as the reactor.

In our process a preferred range of the reaction temperature is from about 70° C. to about 100° C. The intended reaction takes place even at far lower temperatures, but the rate of the reaction is impractically low when the reaction temperature is below 60° C. At 70°-100° C. the rate of the reaction reaches a sufficient level. It is uneconomical to heat the reaction system to a temperature above 100° C. though it has the effect of still enhancing the rate of the reaction, and when the reaction proceeds at such a high temperature the vapor pressure of HFIP formed by reaction becomes so high that the partial pressure of hydrogen lowers considerably while the gas pressure in the reaction system is kept constant.

In the practice of the present invention, usually the hydrogenolysis reaction is carried out in the following manner.

Initially a suitable quantity of a liquid HFA hydrate is charged in a reactor together with a palladium or nickel catalyst, and then the air in the reactor is replaced by hydrogen gas. The HFA hydrate is heated to a desired temperature, and the hydrogen gas pressure in the reactor is adjusted to a desired level. During reaction the liquid in the reactor is stirred well and continuously. Since the reaction is a gas-liquid reaction, efficient stirring makes a great contribution to the enhancement of the rate of the reaction. During reaction hydrogen gas is supplied into the reactor only so as to compensate for the consumption of hydrogen in the reaction to thereby keep the gas pressure practically constant. Therefore, the reaction is carried out with little loss of hydrogen gas.

When the hydrogenolysis of the initially charged HFA hydrate reaches a sufficient degree, the heating and stirring are terminated. After settling of the catalyst to a bottom section of the reactor, a supernatant portion of the reaction liquid is taken out of the reactor as the product, while the hydrogen gas used for the reaction is still confined in the reactor. After that, a suitable quantity of the HFA hydrate is pumped into the reactor to mix with the retained portion of the reaction liquid containing the catalyst, and the reaction is repeated by restarting the heating and stirring. By operating in this manner both the catalyst and hydrogen gas are reused without loss, and the preliminary step of replacing the air in the reactor with hydrogen gas can be omitted at the second operation. In repeating the reaction operation in this way a small portion of the catalyst will be carried away by the recovered product, and the activity of the catalyst gradually lowers. Therefore, it is suitable to replenish the liquid in the reactor with the catalyst at each repetition of the operation in a quantity amounting to about 10% of the initially charged quantity with a view to accomplishing the reaction always at a desirable rate of the reaction and with an invariably good yield of HFIP.

In our process the life of the catalyst or the extent of reusability of the catalyst significantly influences the production cost of HFIP. It is possible to effectively prolong the life of the catalyst used in this process, particularly an active carbon-palladium catalyst, by adding a very small quantity of sodium hydroxide to the HFA hydrate. Then the replenishment of the catalyst in repeating the reaction can be decreased. Furthermore, sodium hydroxide has the effect of enhancing the activity of the catalyst. Usually a suitable quantity of sodium hydroxide is 0.05 to 0.5 wt% of the HFA hydrate. The use of an excessively large quantity of sodium hydroxide will promote side-reactions or excessive hydrogenolytic decomposition the HFA hydrate and will result in a decrease in the yield of HFIP. Some other basic compounds such as calcium hydroxide, sodium carbonate and sodium hydrogen carbonate are also of use for the same purpose, but sodium hydroxide is superior in the effect and is most convenient for practical use.

There is no strict restriction as to the material of the reactor for use in the present invention. Various materials that are fairly resistant to corrosion are of use, and glass, stainless steel, and steel provided with glass lining or polytetrafluoroethylene lining are named as suitable examples. In industrial practice it will be convenient to use a stainless steel reactor or a glass-lined reactor. In the case of a stainless steel reactor, however, the reactor slightly undergoes corrosion during long use and has a tendency to somewhat promote excessive hydrogenolytic decomposition of HFA hydrates. Therefore, it is preferred to use a glass-lined reactor.

Usually the product of the process according to the invention contains a very small amount of free fluorine ions as the result of the hydrogenolytic decomposition of a very small portion of the HFA hydrate to an excessive extent, and sodium hydroxide added for the above described purpose has a tendency to somewhat promote the formation of fluorine ions. It is desirable to suppress the formation of fluorine ions, and this becomes a matter of importance where the reactor is lined with glass. We have found that the formation of fluorine ions for the above reasons can be suppressed to a practically negligible level by adding aluminum hydroxide to the HFA hydrate. It suffices to use a small quantity of aluminum hydroxide. Usually a suitable quantity of aluminum hydroxide is 0.1 to 0.5 wt% of the HFA hydrate. For the same purpose, boric acid, silica, powdery alumina and a mixture of sodium silicate and boric acid are also of use, but aluminum hydroxide is distinctly higher in the effect. There is no harm in using aluminum hydroxide together with sodium hydroxide because neither of these two kinds of additives influences the favorable effect of the other in any way.

The invention will further be illustrated by the following nonlimitative examples.

EXAMPLE 1

Initially, 800 g (3.63 moles) of HFA trihydrate $(CF_3)_2C(OH)_2.2H_2O$ was charged into a 1-liter autoclave which was made of stainless steel (SUS 304) and provided with a stirrer, and an active carbon-palladium catalyst (wetted with water) containing 5 wt% of Pd was added to the HFA hydrate. The dry weight of the catalyst was 8.0 g. The air in the autoclave was replaced by hydrogen gas, and the autoclave was heated in an oil bath to raise the interior temperature to 100° C. Then stirring was started while the hydrogen gas pressure was kept at 4.5 kg/cm$^2$ (gauge pressure). Soon the HFA trihydrate began to vigorously absorb and react with hydrogen. After the lapse of 4.5 hr the heating and stirring were terminated, and the reaction system in the autoclave was left standing for about 12 hr. As the result, 98% of the initially charged HFA trihydrate reacted with hydrogen. In this reaction the selectivity factor for HFIP was 100%. That is, the reaction product was 800 g of aqueous solution of HFIP containing a small amount of unreacted HFA hydrate. In this reaction product the presence of 150 ppm of fluorine ions was detected.

A major and supernatant portion of the reaction product was discharged from the autoclave to leave 200 g of the reaction product and the entire quantity of the catalyst in the autoclave. Then, 800 g of HFA trihydrate and 0.8 g (dry weight) of the active carbon-palladium catalyst were additionally charged into the autoclave, and the above described hydrogenolysis reaction was carried out in the same manner. In 6.0 hr the degree of reaction of the HFA hydrate reached 97%, and the selectivity factor for HFIP was 100%. Thus, it was evidenced that the catalyst is reusable.

EXAMPLE 2

The hydrogenolysis reaction of Example 1 was carried out in the same manner except that aluminum hydroxide amounting to 0.5 wt% of HFA trihydrate was added together with the catalyst. In 6 hr the degree of reaction of the HFA hydrate reached 99.3%, and the selectivity factor for HFIP was 100%. In this case the concentration of fluorine ions in the reaction product was only 10 ppm.

EXAMPLE 3

The hydrogenolysis reaction of Example 1 was carried out in the same manner except that sodium hydroxide amounting to 0.3 wt% of HFA trihydrate was added together with the catalyst. In 4.5 hr the degree of reaction of the HFA hydrate reached 98%, and the selectivity factor for HFIP was 99.2% so that the obtained HFIP solution contained 0.8% of by-products (b.p 76° C.).

The catalyst was reused several times, each time in the manner as described in Example 1. In the reaction at the fifth time the catalyst still exhibited sufficient activity, so that the degree of reaction of HFA trihydrate reached 96% in 8 hr with 99.5% selectivity for HFIP. In the products of the repeated reaction the concentrations of fluorine ions were 500 to 2000 ppm. Distillation of the crude HFIP obtained in this experiment gave refined HFIP with purity of above 99.99%.

EXAMPLE 4

Initially, 99 kg (0.45 kilomoles) of HFA trihydrate $(CF_3)_2C(OH)_2.2H_2O$ (d≈1.59) was charged into a 100-liter reactor, which was made of a stainless steel (SUS 316) and provided with a stirrer, together with 126 g (0.13 wt% of the HFA hydrate) of sodium hydroxide and 495 g (0.5 wt% of the HFA hydrate) of aluminum hydroxide. After the addition of 906 g of an active carbon-palladium catalyst containing 5 wt% of Pd (wetted with water, dry weight 495 g, 0.5 wt% of the HFA hydrate), the air in the reactor was replaced by hydrogen gas. The temperature in the reactor was raised to 70° C. Then stirring was started, and hydrogen gas was introduced into the reactor such that the hydrogen gas pressure at the start of the reaction became 2.0 kg/cm$^2$ (gauge pressure). The reaction between HFA trihydrate and hydrogen proceeded rapidly. Since this reaction was exothermic the reaction temperature rised up to 80° C. In 4 hr the degree of reaction of the HFA hydrate reached 80%, while the rate of consumption of hydrogen per unit time lowered appreciably. Then the hydrogen gas pressure in the reactor was raised to 4.5 kg/cm$^2$ (gauge pressure). After the lapse of 6 hr the stirring and the feed of hydrogen gas were terminated, and the reaction system in the reactor was left standing for about 12 hr. As the result, 99.1% of the initially charged HFA trihydrate reacted with hydrogen gas, and the selectivity factor for HFIP was 99.7%. As to hydrogen, 99% of the used hydrogen gas reacted with the HFA hydrate. In the obtained HFIP solution the concentration of fluorine ions was 10 ppm.

EXAMPLE 5

The hydrogenolysis reaction of Example 4 was carried out in the same manner except that 190 g of a Raney nickel catalyst (wetted with water) was used in place of the carbon-palladium catalyst. In 9 hr the degree of reaction of HFA trihydrate reached 68.5%, and the selectivity factor for HFIP was 100%.

What is claimed is:

1. A process for preparing 1,1,1,3,3,3-hexafluoropropane-2-ol, comprising the steps of adding to a hexafluoroacetone hydrate 0.1 to 0.5% aluminum hydroxide by weight of said hexafluoroacetone hydrate and contacting the mixture of hexafluoroacetone hydrate and aluminum hydroxide with hydrogen gas in the liquid phase in the presence of a catalyst which is active for hydrogenolysis of said hexafluoroacetone hydrate into 1,1,1,3,3,3-hexafluoropropane-2-ol.

2. A process according to claim 1, wherein said catalyst comprises metallic palladium.

3. A process according to claim 2, wherein said catalyst further comprises active carbon on which said palladium is deposited.

4. A process according to claim 3, wherein the content of metallic palladium in said catalyst is in the range from 2 to 5% by weight.

5. A process according to claim 4, wherein the quantity of said catalyst is in the range from 0.1 to 1.0% by weight of said hexafluoroacetone hydrate.

6. A process according to claim 1, wherein said catalyst comprises metallic nickel.

7. A process according to claim 1, wherein the gauge pressure of said hydrogen gas is in the range from 2 to 10 kg/cm$^2$.

8. A process according to claim 7, wherein the hydrogenolysis reaction temperature is in the range from about 70° C. to about 100° C.

9. A process according to claim 1, further comprising the step of adding sodium hydroxide to said hexafluoroacetone hydrate before starting the hydrogenolysis reaction.

10. A process according to claim 9, wherein the quantity of said sodium hydroxide is in the range from 0.05 to 0.5% by weight of said hexafluoroacetone hydrate.

11. A process according to claim 1, wherein said hexafluoroacetone hydrate is expressed by the formula $(CF_3)_2C(OH)_2 \cdot xH_2O$, where x is a number larger than 0.5.

12. A process according to claim 11, wherein x in the formula is 2.

* * * * *